US011607385B2

(12) United States Patent
Halbherr et al.

(10) Patent No.: US 11,607,385 B2
(45) Date of Patent: Mar. 21, 2023

(54) LIPOSOMES COMPRISING SPHINGOMYELIN

(71) Applicant: INNOMEDICA HOLDING AG, Zug (CH)

(72) Inventors: Stéfan Jonathan Halbherr, Bern (CH); Camille Peitsch, Bern (CH)

(73) Assignee: INNOMEDICA HOLDING AG, Zug (CH)

( * ) Notice: Subject to any disclaimer, the term of this patent is extended or adjusted under 35 U.S.C. 154(b) by 24 days.

(21) Appl. No.: 16/956,239

(22) PCT Filed: Dec. 20, 2018

(86) PCT No.: PCT/EP2018/086352
§ 371 (c)(1),
(2) Date: Jun. 19, 2020

(87) PCT Pub. No.: WO2019/122220
PCT Pub. Date: Jun. 27, 2019

(65) Prior Publication Data
US 2021/0077398 A1    Mar. 18, 2021

(30) Foreign Application Priority Data
Dec. 21, 2017 (EP) .................................... 17209738

(51) Int. Cl.
*A61K 9/127* (2006.01)
*A61K 9/00* (2006.01)
(52) U.S. Cl.
CPC .......... *A61K 9/1272* (2013.01); *A61K 9/0019* (2013.01)

(58) Field of Classification Search
None
See application file for complete search history.

(56) References Cited

U.S. PATENT DOCUMENTS

| 4,247,547 A * | 1/1981 | Marks ................... A61K 8/671 |
| | | 424/78.05 |
| 2005/0137223 A1 | 6/2005 | Fan et al. |
| 2007/0154539 A1* | 7/2007 | Fountain .................. A61K 8/67 |
| | | 977/907 |

(Continued)

FOREIGN PATENT DOCUMENTS

| CN | 1833633 A | 9/2006 |
| WO | 2007/044748 A2 | 4/2007 |

(Continued)

OTHER PUBLICATIONS

Elisa Salvati et al. "Liposomes functionalized to overcome the blood-brain barrier and to target amyloid-β. peptide: the chemical design affects the permeability across an in vitro model. "International Journal of Nanomedicine, vol. 8, 2013, pp. 1749-1758. (Year: 2013).*

(Continued)

*Primary Examiner* — Isaac Shomer
(74) *Attorney, Agent, or Firm* — Finch & Maloney PLLC (57) ABSTRACT

Liposomes which comprise sphingomyelin in the lipid bilayer. The liposomes are configured to cross the blood-brain barrier for the treatment of neuro-degenerative diseases and spinal cord injuries. The liposomes are essentially free of ganglioside. A method of producing liposomes is also disclosed along with use of liposome as a medicament.

16 Claims, 9 Drawing Sheets

(56) References Cited

U.S. PATENT DOCUMENTS

| | | | | |
|---|---|---|---|---|
| 2013/0216606 A1* | 8/2013 | Venkatraman | ......... | A61K 9/127 514/530 |
| 2014/0004172 A1* | 1/2014 | Masserini | ............ | A61K 9/1277 514/17.7 |

FOREIGN PATENT DOCUMENTS

| | | | | |
|---|---|---|---|---|
| WO | 2008/033253 | A2 | 3/2008 | |
| WO | 2009/150686 | A1 | 12/2009 | |
| WO | WO-2009150686 | A1 * | 12/2009 | ............ A61K 47/24 |
| WO | 2013/018091 | A1 | 2/2013 | |
| WO | 2014/000857 | A1 | 1/2014 | |

OTHER PUBLICATIONS

Shraddha D. Rege, Thangiah Geetha, Gerald D. Griffin, Tom L.Broderick, and Jeganathan Ramesh Babu. "Neuroprotective effects of resveratrol in Alzheimer disease pathology." Frontiers in Aging Neuroscience, vol. 6 Article 218, Sep. 2014, pp. 1-12. (Year: 2014).*
Renzo Mancuso et al. "Resveratrol Improves Motoneuron Function and Extends Survival in SOD1G93AALS Mice." Neurotherapeutics, vol. 11, 2014, pp. 419-432. (Year: 2014).*
Débora B Vieira Lionel F Gamarra. "Getting into the brain: liposome-based strategies for effective drug delivery across the blood-brain barrier." International Journal of Nanomedicine, vol. 11, 2016, pp. 5381-5414. (Year: 2016).*
Claudia Balducci et al. "Multifunctional Liposomes Reduce Brain B-Amyloid Burden and Ameliorate Memory Impairment in Alzheimer's Disease Mouse Models." The Journal of Neuroscience, Oct. 15, 2014, vol. 34(42), pp. 14022-14031. (Year: 2014).*
Laura Bana et al. "Liposomes bi-functionalized with phosphatidic acid and an ApoE-derived peptide affect Aβ aggregation features and cross the blood-brain-barrier: Implications for therapy of Alzheimer disease." Nanomedicine: Nanotechnology, Biology, and Medicine vol. 10 (2014) pp. 1583-1590. (Year: 2014).*
Elisa Salvati et al. "Liposomes functionalized to overcome the blood-brain barrier and to target amyloid-8 peptide: the chemical design affects the permeability across an in vitro model. "International Journal of Nanomedicine, vol. 8, 2013, pp. 1749-1758. (Year: 2013).*
Malka Shilo, Anat Sharon, Koby Baranes, Menachem Motiei, Jean-Paul M Lellouche and Rachela Popovtzer. "The effect of nanoparticle size on the probability to cross the blood-brain barrier: an in-vitro endothelial cell model." Journal of Nanobiotechnology, vol. 13:19, 2015, pp. 1-7. (Year: 2015).*
Chandraprakash Dwivedi, Shekhar Verma. "Review on Preparation and Characterization of Liposomes with Application." Journal of Scientific & Innovative Research, vol. 2, Issue 2, Mar.-Apr. 2013, pp. 486-508. (Year: 2013).*
James C. Dodge et al. "Glycosphingolipids are modulators of disease pathogenesis in amyotrophic lateral sclerosis." Proceedings of the National Academy of Sciences, vol. 112 No. 26, Jun. 30, 2015, pp. 8100-8105. (Year: 2015).*
Andrew D. Wong et al. "The blood-brain barrier: an engineering perspective." Frontiers in Neuroengineering, vol. 6 Article 7, 2013, pp. 1-22. (Year: 2013).*
C. Saraiva et al., "Nanoparticle-mediated brain drug delivery: Overcoming blood-brain barrier to treat neurodegenerative diseases", Journal of Controlled Release, 235, May 18, 2016, pp. 34-47, See Spec., p. 2.
R. Meir et al., "Design principles for noninvasive, longitudinal and quantitative cell tracking with nanoparticle-based CT Imaging", Nanomedicine: Nanotechnology, Biology and Medicine, vol. 13, Issue 2, Feb. 2017, pp. 421-429, See Spec., p. 2.
C. Sacks et al., "The Failure of Solanezumab—How the FDA Saved Taxpayers Billions", New England Journal of Medicine, 2017; 376, pp. 1706-1708, See Spec., p. 2.
A. Abbot et al., "Leading Alzheimer's theory survives drug failure", News in Focus, vol. 54, Nature, Dec. 1, 2016, pp. 15-16, See Spec., p. 2.
E. Siemers et al., "Phase 3 solanezumab trials: Secondary outcomes in mild Alzheimer's disease patients", Alzheimer's & Dementia, 12 (2016) pp. 110-120, See Spec., p. 3.
J. Schneider et al., "A randomized, controlled, delayed start trial of GM1 ganglioside in treated Parkinson's disease patients", Journal of the Neurological Science, vol. 324, Issues 1-2, Jan. 15, 2013, pp. 140-148, See Spec., p. 4.
D. Lammertse, "Clinical trials in spinal cord injury: lessons learned on the path to translation. The 2011 International Spinal Cord Society Sir Ludwig Guttmann Lecture", Spinal Cord, 51, Nov. 2-9, 20,2012, See Spec., p. 4.
H. Huang et al., Clinical Neurorestorative Therapeutic Guidelines for Spinal Cord Injury (INAR/CANR version 2019), Journal of Orthopaedic Translation, 20, Nov. 11, 2019, pp. 14-24, See Spec., p. 4.
T. Ariga., "The Pathogenic Role of Ganglioside Metabolism in Alzheimer's Disease-Cholinergic Neuron-Specific Gagliosides and Neurogenesis", Molecular Neurobiology, 54, Jan. 9, 2016, pp. 623-638, See Spec., p. 7.
S. Ong et al., "Evaluation of Extrusion Technique for Nanosizing Liposomes", Pharmaceutics, 8, 36, Dec. 21, 2016, pp. 1-12, See Spec., p. 9 & 14.
M. Aurélio et al., "Traumatic Injuries of the Cervical Spine: Current Epidemiological Panorama", Original Article, Acto Ortop Bras. 2018; 26(2), pp. 123-126, See Spec., p. 11.
Y. Perrie et al., "Manufacturing Methods for Liposome Adjuvants", Methods in Molecular Biology, vol. 1494, Oct. 8, 2016, pp. 127-144, See Spec., p. 14.
R. Ledeen et al., "The multi-tasked life of GM1 ganglioside, a true factotum of nature", CellPress, Special Issue: The Magic of the Sugar Code, Trends in Biochemical Sciences, vol. 40, No. 7, Jul. 2015, pp. 407-418.
N. Haughey, "Sphingolipids in Neurodegeneration", Neuromolecular Medicine, 12(4), Dec. 2010, pp. 301-305.
A. Kharlamov et al., "Semisynthetic Sphingolipids Prevent Protein Kinase C Translocation and Neuronal Damage in the Perifocal Area following a Photochemically Induced Thrombic Brain Cortical Lesion", The Journal of Neuroscience, 13(6), Jun. 1993, pp. 2483-2494.
Z. Jones et al., "Sphigolipids in spinal cord injury", Int. J. Physiol Pathophysiol Pharmacol, 8(2), Aug. 15, 2015, pp. 52-69.
E. Posse de Chaves et al., "Sphingolipids and gangliosides of the nervous system in a membrane function and Tysfunction", FEBS Letters, 584, Dec. 17, 2009, pp. 1748-1759.
European Search Report Corresponding to 17209738.8 dated Jun. 1, 2018.
International Search Report Corresponding to PCT/EP2018/086352 dated Mar. 14, 2019.
Written Opinion Corresponding to PCT/EP2018/086352 dated Mar. 14, 2019.
Agrawal Mukta et al., "Recent Advancements in Liposomes Targeting Strategies to Cross Blood-Brain Barrier (BBB) for the Treatment of Alzheimer's Disease", Journal of Controlled Release, Elsevier, Amsterdam, Netherlands, vol. 260, May 24, 2017, pp. 61-77, See European Action.
M. Danaei et al., "Impact of Particle Size and Polydispersity INdex on the Clinical Applications of Lipidic Nanocarrier Systems", Pharmaceutics, vol. 10, No. 2, May 18, 2018, p. 57, See European Search.
Magro Roberta Dal et al., "The Ability of Liposomes, Tailored for Bood-Brain Barrier Targeting, to Reach the Brain is Dramatically Affected by the Disease State",Nanomedicine, vol. 13, No. 6, Jan. 29, 2018, pp. 585-594, See European Action.
European Office Action Corresponding to 18825700.0 dated Sep. 24, 2021.

* cited by examiner

LIPOSOMES COMPRISING SPHINGOMYELIN

The present invention relates to liposomes, a method of producing liposomes and liposomes for the use as a medicament.

A liposome is a spherical vesicle having at least one lipid bilayer. Liposomes may also be multivesicular liposomes in which one vesicle contains one or more smaller vesicles. The liposome has an aqueous solution core surrounded by a hydrophobic membrane in the form of a lipid bilayer.

The use of liposomes for drug delivery has been proposed for a variety of drugs, particularly those which are administered parenterally. Liposomes have the potential to provide controlled "depot" release of the administered drug over an extended time period, and to reduce side effects of the drug, by limiting the concentration of free drug in the bloodstream. Liposomes can also alter the tissue distribution and uptake of drugs, in a therapeutically favorable way, and can increase the convenience of therapy, by allowing less frequent drug administration. For example, liposomes may transport encapsulated active components directly to the disease site, including tumour cells and sites of inflammation. The active component can be directly released from the liposome at the treatment site. Thus, a lower dosage of the active component is required, and side effects are in consequence limited.

However, depending on the targeted cells, the liposomes need to be modified in order to assure the release of the medicament at the desired treatment site.

The development of drug delivery systems to treat neurodegenerative diseases and spinal cord injuries is particularly challenging, as such systems need to reach the brain and/or the spinal cord. However, due to the restrictive nature of the blood-brain barrier, a special layer of tissue constituting a protective barrier between the central nervous system and the systemic blood circulation, the development of such systems remains rather challenging.

Different efforts have been made in the past to treat neurodegenerative diseases with liposomes. WO 2014/000857 describes the use of liposomes comprising phosphatidic acid and/or cardiolipin as well as apolipoprotein E (ApoE) as the active component in the treatment of Alzheimer's disease. Even though amyloid plaque formation associated with Alzheimer's disease can be reduced at the extra- and intracellular level of the limbic system upon treatment with such liposomes, accumulating evidence from human clinical trials suggests that plaque formation is rather a symptom of disease but not the cause. Multiple phase 3 clinical studies have failed to demonstrate that eliminating plaques slows down disease progression in humans. Recent scientific literature suggests that the particle size of 100 nm described in WO 2014/000857 is too large to efficaciously pass the blood-brain barrier (Saraiva C. et al. 2016 J Controlled Release; Betzer O. et al. 2017 Nanomedicine (London)).

In the example of Alzheimer's disease, further efforts to develop treatment have been undertaken. One recent example is the development of an antibody-based therapy against Alzheimer intending to clear beta-amyloid plaques. However, accumulating evidences from clinical trials suggest that monoclonal antibodies aiming at amyloid-beta clearance do not provide benefits to Alzheimer patients (N Engl J Med. 2017 May 4; 376(18): 1706-1708. and Nature. 2016 Nov. 23; 540(7631): 15-16. and Alzheimers Dement. 2016 Feb; 12(2): 110-120. Therefore, the need to find alternative approaches for the treatment of Alzheimer's disease persists.

WO 2008/033253 A2 describes the use of liposome complexes for delivering pharmaceutical agents across the blood-brain barrier for the treatment of neurodegenerative diseases. The liposomes are prepared from phospholipids and are associated with a pharmaceutical agent. Further, the liposomes are modified with sialic acid-containing molecules, such as gangliosides, attached to the liposomes. The sialic acid-containing molecule may serve as a linker between the targeting agent, such as antibody based agents or peptides analogues, and the external surface of the liposome or may be attached to the external surface of the liposome to prevent scavenging of the liposome by the body's reticulo-endothelial system. In any case, according to WO 2008/033253, sialic acid-containing molecules are required for ensuring transportation of the targeting agent to the brain.

WO2007/044748 discloses a pharmaceutical composition of liposomes containing sphingomyelin to treat disorders involving neuropathic pain and aberrant muscle contractions associated with bladder hyperactivity disorders. The liposomes are produced by thin film hydration.

WO2009/150686 discloses liposomes which are capable of effectively binding beta amyloid peptide and are useful for the treatment, prevention and diagnosis of Alzheimer's disease. The liposomes are produced by extrusion.

The drawback of such liposomes is a rather laborious and costly industrial scale production. Moreover, the targeting moiety—chemically linked to the liposomal surface—may generate body-foreign molecular structures, which are likely immunogenic and may provoke adverse drug reactions. In contrast, the liposomal membrane of the invention described in this patent application is essentially free of body-foreign molecules, resulting in high biocompatibility.

Another problem lies with the administration of certain active components such as the neuroprotector GM1 ganglioside for the treatment of neurodegenerative diseases. For example, the administration of ganglioside GM1 for indications such as Parkinson's disease has been described to cause difficulties in treatment (J. Neurol. Sci. 2013; 324(1-2): 140-148). Furthermore, the treatment of spinal cord injuries using free GM1 has shown positive outcomes in patients (Spinal Cord (2013) 51, 2-9 and Acta Ortop Bras. 2016 May-June; 24(3): 123-6). Due to the pharmacokinetics of GM1, the substance has to be administered subcutaneously or intravenously at high doses. The high dose and route of administration make patients prone to certain types of adverse reactions, such as local pain and swelling at the site of injection, erythema, pruritus and hematoma. It is desirable to avoid such side effects and to avoid the use of high amounts of GM1.

Therefore, there is an unmet medical need for an effective drug delivery systems, which can transport active components to the brain and to the spinal cord for the treatment of neurodegenerative diseases, spinal cord injuries and other neurological disorders. There is in particular a need to provide delivery systems that can overcome the restrictive mechanism imposed by the blood-brain barrier. Ideally, the delivery system can be administered non-parenterally, thus avoiding the risks and inconveniences associated with parenteral administration.

It is thus an object of the present invention to address those needs and to provide liposomes suitable as active components and/or as carrier systems in the treatment of neurodegenerative diseases and spinal cord injuries. It is another object of the present invention to provide a method of producing such liposomes and provide the use of such liposomes as a medicament.

The objects have been solved by liposomes, a method for producing liposomes and liposomes for the use as medicament as outlined below.

The invention relates to liposomes, which comprise sphingomyelin (SM) in the lipid bilayer and are essentially free of gangliosides. In particular, the lipid bilayer of the liposome is essentially free of gangliosides. The liposomes are configured to cross the blood-brain barrier and are suitable for the treatment of neurodegenerative diseases and spinal cord injuries. The different properties of the liposome which render it suitable to configure the blood-brain barrier are described below in more detail.

Sphingomyelin belongs to the group of phospholipids and sphingolipids. It makes up about 10% of the lipids of the brain. Sphingomyelin tends to be in greatest concentrations in the plasma membrane, and especially in the outer leaflet, of cells.

Figure 4:
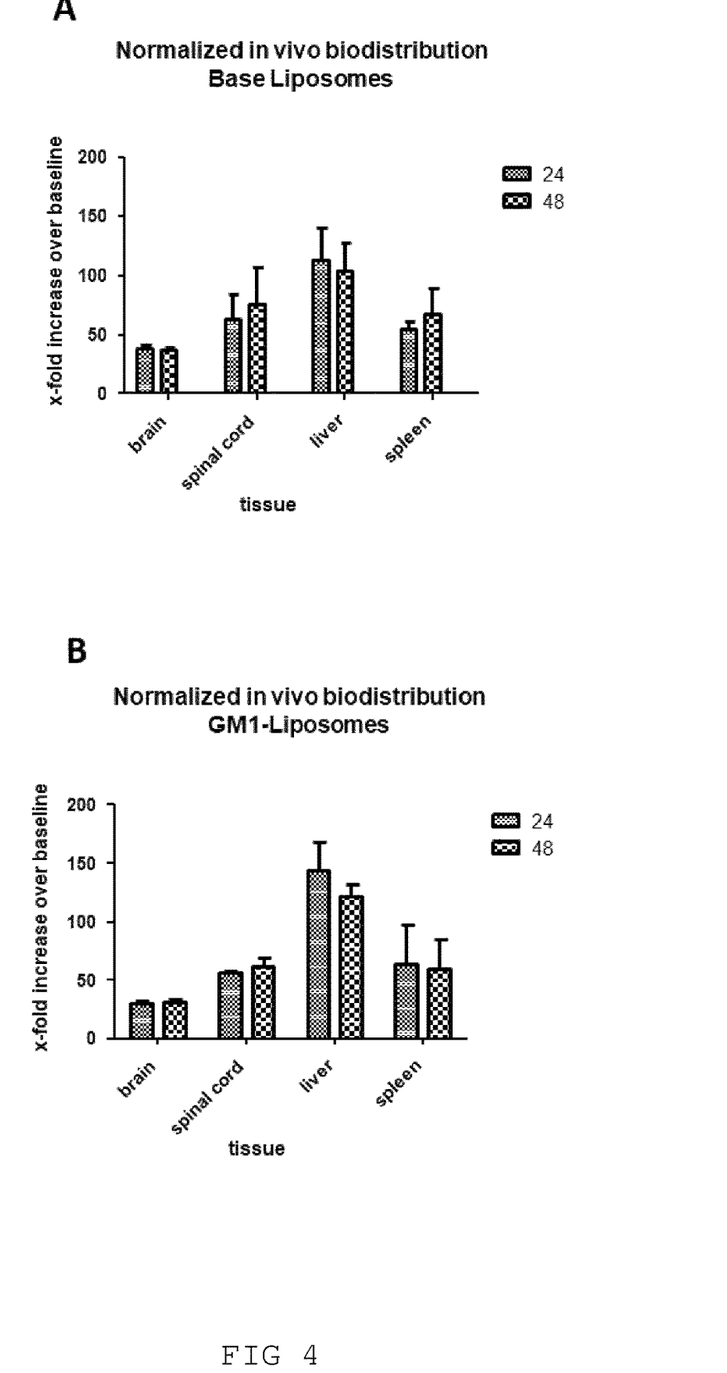
FIG. 4: Graphic representation of the biodistribution analysis in the brain, spinal cord, liver and spleen from the in vivo biodistribution images of FIGS. 2 and 3.

Liposomes comprising sphingomyelin as described in this invention show enhanced stability and enhanced biological properties. These liposomes can act as a medicament. The liposomes may also act as drug carrier system with enhanced pharmacokinetics and therapeutic properties. Surprisingly, it was found that liposomes essentially free of gangliosides are very efficient in crossing the blood-brain barrier and, after administration, can be found in the brain and spinal cord. Moreover, it has been demonstrated that the crossing efficacy is increased compared to liposomes comprising a significant amount of ganglioside (FIG. 4). Thus, an additional modification with ganglioside is not necessary to cross the blood-brain barrier. The liposomes according to the invention are exceptionally suitable as medicament and/or drug carriers for active components directed to the treatment of neurodegenerative diseases and spinal cord injuries.

"Essentially free" in the context of the invention refers to an amount of ganglioside less than 5% mol, preferably even less than 3% mol and most preferably less than 1% mol. It may also be that the liposomes are free of ganglioside.

Sphingomyelin used for the purpose of the present invention can be obtained either by way of synthesis or by way of extraction from natural based components, in particular components of animal origin. Preferably, the sphingomyelin used for the purpose of the present invention is Palmitoyl-D-erythro-sphingosine-1-phosphocholine. Palmitoyl-D-erythro-sphingosine-1-phosphocholine corresponds to the body's own sphingomyelin type phospholipids (d18:1/16:0), resulting in an improved uptake of the liposome into the body, and in particular into the brain and spinal cord. Furthermore, its C16 chain provides a high liposomal stability.

It was further found that the liposomes can be metabolized in clearing organs such as spleen and liver and are thus removed from the body after treatment, avoiding long-term accumulation.

The liposomes may additionally comprise cholesterol (Chol). Preferably, the ratio of sphingomyelin and cholesterol in the liposome may vary between 60-40% mol and 45-55% mol respectively. Liposomes comprising sphingomyelin and cholesterol show an enhanced circulation lifetime. They have improved pharmacokinetics and therapeutic characteristics. They are biocompatible and biodegradable. Sphingomyelin-cholesterol interaction may lead to cholesterol/sphingolipid-enriched nano- and micro-domains (referred to as membrane "rafts") in the plane of plasma and other organelle (e.g. Golgi) membrane. These domains play an important role in regulating synaptic functions and synapse formation, neurotransmitter release and synaptic plasticity (Mol Neurobiol. 2017 Jan; 54(1): 623-638).

The liposomes may essentially be free of surface modifications. By "essentially free" in the context of the modification, it is meant that the modification constitute less than 5% mol of the liposome, preferably even less than 3% mol and most preferably less than 1% mol. The liposome may also be completely free of surface modifications. The surface modification referred to are folic acid, peptides, antibodies, sugars, polyethylene glycol, monoclonal antibodies, fractions of monoclonal antibodies or surface proteins.

Side effects, caused by such modification, can thus be avoided. With this present innovation, a smaller liposomal diameter can be reached allowing a facilitated crossing of the blood-brain barrier. Moreover, the risks of an immune reaction may be lower when the body's own lipids are used. Liposomes without surface modification provide in this case a higher biological compliance avoiding amongst others an enhanced clearance rate. According to the current state of the art, the liposomal surface modification and active targeting is technically very challenging, which may also lead to inefficient biodistributions and lower cost benefit ratio. Further relevant aspects of the present invention may not only be the reduced costs but also the amount of manufacturing steps leading to a facilitated large-scale production.

GM1 is known as neuroprotector. Further, GM1 may interact with a number of proteins that form precipitates in diseases of the central nervous system (CNS) including alpha-synuclein (Parkinson's disease), amyloid-beta (Alzheimer's disease), and huntingtin (Huntington's disease). GM1 and its derivatives are known to penetrate the blood-brain barrier and the neuronal plasma membrane. Administration of LIGA20, a derivative of GM1 has also been demonstrated to reduce Parkinson's symptoms in a rodent model of Parkinson's disease.

Thus, GM1 and derivatives may be inserted in the aqueous compartment of the liposome as an active component in the treatment of neurodegenerative diseases and spinal cord injuries. If incorporated as active component into the aqueous phase of the liposome, GM1 may be present in an amount between 5 and 15% mol, preferably 9 to 11% mol and most preferably 10% mol.

The surface charge of the liposome is an important consideration in the preparation of liposome formulations and a first analytical indication on the insertion of ganglioside GM1. If the ganglioside GM1 is inserted into the liposomal lipid bilayer, the liposome shows a more negative Zeta-potential than the base vesicle lipid bilayer constituted of sphingomyelin and cholesterol. The Zeta-potential can be analysed using a DLS-device and lies in the range of −10 to −60 mV. Liposomes with SM/Chol show a Zeta-potential of −10 mV, SM/Chol/GM1 liposomes show a Zeta-potential of −49 mV. GM1 is negatively charged at pH≥5, thus liposomes carrying GM1 become negatively charged. By measuring the Zeta-potential, it can be determined whether the liposome is essentially free of gangliosides.

Preferably, the liposomes have a mean diameter between 10 and 70 nm, preferably between 10 and 50 nm and most preferably 25 to 35 nm. The mean diameter is determined by cryo transmission electron microscopy (cryoTEM) with a standard deviation of approx. 10 nm.

Liposomes of a mean diameter not exceeding 50 nm are more likely to pass the blood-brain barrier. In addition, they are opsonized less rapidly and at a lower extent than their larger counterparts and are cleared less rapidly by the reticuloendothelial system.

It is preferred that formulations based on such liposomes have a polydispersity index of 0.15, more preferably a polydispersity index from 0.10 to 0.15, and are therefore essentially monodisperse. The polydispersity index is determined by dynamic light scattering (DLS). A polydispersity index 0.15 is superior over the polydispersity indices of liposomal formulations known in the art. Liposomal formulations known in the art, available by extrusion, homogenization, and sonication procedures, typically show polydispersity indices of 0.2 to 0.4 (Gim Ming Ong et al., Evaluation of Extrusion Technique for Nanosizing Liposomes, Pharmaceutics 2016 (8) 36, p. 5). Essentially monodisperse liposomal formulations are beneficial for reproducibility purposes, industrial scale production and compliant with marketing authorization requirements.

The circularity and the lamellarity of the liposomes in a formulation are determined by cryo transmission electron microscopy (cryoTEM). Preferably, the liposomes have a relative circularity of 0.95 and most preferably of 0.98 to 1.00. A circularity of 1.00 represents an absolute circle according to the standard physic rules. Preferably, the liposomes are unilamellar and hold one inner compartment. The liposomes of a liposomal formulation according to the invention are preferably to 90% unilamellar and most preferably 97% to 99% unilamellar.

A homogeneous circularity and unilamellarity of the liposomal dispersion provides a controlled and industrially scalable manufacturing process.

Figure 7:
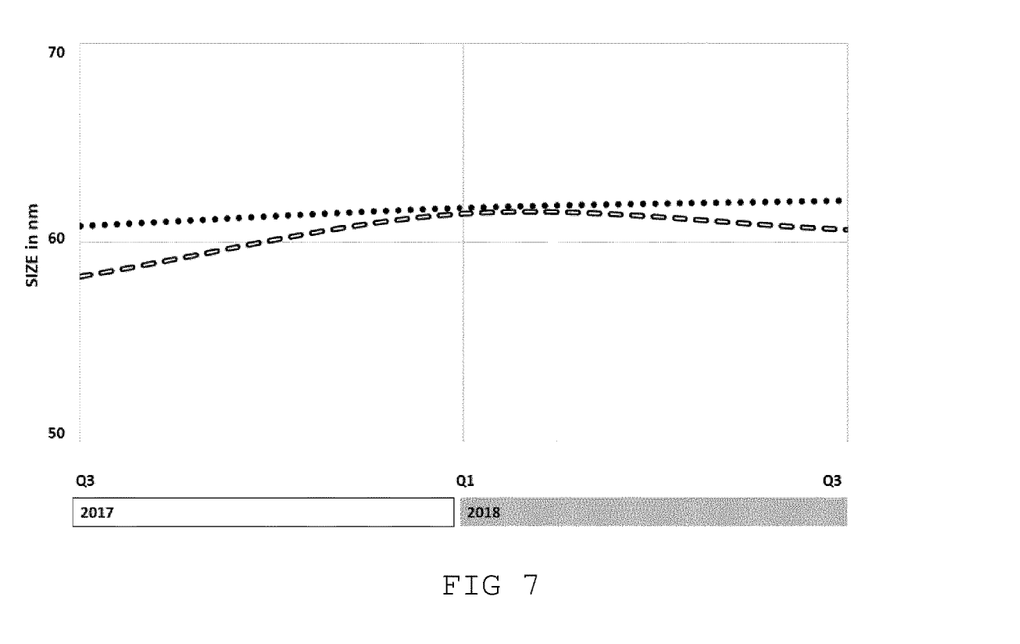
FIG. 7: Characterization of size stability of the liposomes over time, measured by dynamic light scattering DSC.

In a preferred embodiment of the invention, the mean diameter of a formulation based on liposomes according to the invention after 6 months, preferably after 12 months, from manufacturing is between 10 and 70 nm, preferably between 10 and 50 nm and most preferably 25 to 35 nm. It is particularly preferred that the mean diameter of the liposomes in a formulation after 6 months, preferably after 12 months from manufacturing is essentially the same as the mean diameter of the liposomes in the formulation immediately after manufacturing (FIG. 7).

Figure 8:
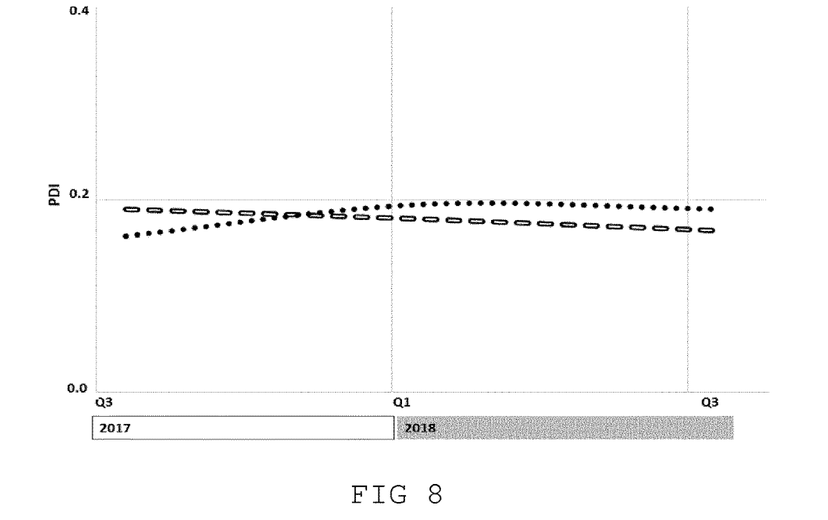
FIG. 8: Characterization of polydispersity stability of the liposomes over time, measured by dynamic light scattering DSC.

In a preferred embodiment of the invention, the polydispersity index of a formulation based on liposomes according to the invention after 6 months, preferably after 12 months from manufacturing is ≤0.15, preferably 0.1 to 0.15. It is particularly preferred that the polydispersity index of the liposomes after 6 months, preferably after 12 months, from manufacturing is essentially the same as the polydispersity index of the liposomes immediately after manufacturing (FIG. 8).

The liposomes according to the invention are thus particularly stable. The controllability and longevity of the size of liposomes is beneficial for manufacturing, storage, shelf life and patient safety proposes.

The neurodegenerative disease treatable with the liposomes may be chosen from the group: tauopathies, in particular Alzheimer's disease; synucleinopathies, in particular Parkinson's disease;

trinucleotide repeat disorder, in particular Chorea Huntington; motor neurone disease, in particular amyotrophic lateral sclerosis; prion diseases, in particular Creutzfeldt-Jakob Disease; diseases of the central nervous system, in particular multiple sclerosis.

Spinal cord injuries as used in the context of the invention refer to all types of spinal cord injuries, complete and incomplete ones.

Spinal cord injuries can be addressed with the liposome of this invention, preferably with the addition of ganglioside, for example GM1, in the inner aqueous compartment of the liposome. GM1, as a neuroprotector, has been shown to restrain the secondary damages (co lateral biochemical damages triggered upon cell death) upon primary damages (mechanical damages). Furthermore, it has been observed to partially restore the sensory part of the concerned area(s) (Acta Ortop Bras. 2016 May-June; 24(3): 123-6).

Preferably, at least one active component is comprised and/or encapsulated in the liposomes. It may be also possible to comprise or encapsulate more than one active component. For example, it is possible to comprise or encapsulate active components that show a synergistic effect upon release. At least one active component can also be comprised in the liposomal bilayer and another at least one active component can be encapsulated in the same liposome. It is further possible, that the liposomes are in the form of multivesicular liposome and wherein different active components form part of the same or different smaller vesicles in the multivesicular liposome.

By "comprised in the liposome" it is meant that the active component forms part of the lipid bilayer or is incorporated in the lipid bilayer, respectively. By "encapsulated in the liposome" it is meant, that the active component is enclosed in the inner aqueous compartment of the vesicle.

The term "active component" may include pharmacologically active drugs as well as pro-drugs. Pro-drugs are medications or compounds that, after administration, are metabolized into pharmacologically active drugs.

The active component can be selected from the group consisting of small or large organic or inorganic molecules, nucleic acids, nucleic acids analogues and derivatives, peptides, peptidomimetics, protein, antibodies and antigen binding fragments thereof, monosaccharides, disaccharides, trisaccharides, oligosaccharides, lipids, glycosaminoglycans, an extract made from biological material, and any combination thereof.

The liposome itself can also be an active component, loaded and unloaded.

Those kinds of liposomes offer a broad range of applications.

The advantage of liposomes comprising or encapsulating active components can be found in an enhanced therapeutic effect. The liposomes may transfer the active components to the site of action. Since the liposomal membrane is structurally similar to biological membranes, the liposomes may merge with the cellular membranes. Upon merging, the liposomal contents may be emptied into the cell where the active component can act. The use of liposomes as drug carrier system may reduce the side effects associated with the administration of the respective active component and related to high systematic absorption of the active component. The active component can be accumulated at the desired target. The components of the liposome bilayer may be metabolised in the liver and/or spleen.

Preferably, the active component is chosen from the group, consisting of: cholinesterase-inhibitors, in particular donepezil or tacrine; dopamine agonist, in particular bromocriptin or pramipexol; resveratrol; nicotinic derivatives, in particular nicotinamide, nicotinic acid, niacin or NAD+.

Sphingomyelin and/or cholesterol can be chosen as active components too.

In a preferred embodiment of the invention, at least gangliosides, in particular GM1 gangliosides, are encapsulated in the liposome as an active component.

A further aspect of the invention is a method for producing liposomes, preferably liposomes as previously described. The method comprises the steps of:

a) providing lipids and cholesterol in an organic solvent,
b) adding an aqueous liquid, c) sonication to enable liposome formation,
d) optionally: separating the liposomes, Step c) is carried out such that the liposomes have a mean diameter between 10 and 70 nm, preferably 10 to 50 nm and most preferably 25 to 35 nm, measured by cryo transmission electron microscopy (cryoTEM).

Preferably, the lipids and cholesterol in the organic solvent provided in step a) are not subjected to thin film hydration. By "thin-film hydration" a conventional method for the preparation of liposomes, involving the step of making a thin lipid film in a round-bottom flask by the removal of organic solvent, is meant. Using this method, heterogeneous liposomes are formed upon the addition and agitation of a dispersion medium. Finally, after extrusion through polycarbonate membranes, homogeneous small liposomes are obtained.

In a preferred embodiment of the invention, the liposomes are not subject to a surface modification step, such that the liposomes are essentially free of surface modifications. By "surface modification step" is meant incorporation of folic acid, peptides, antibodies, sugars, polyethylene glycol, monoclonal antibodies, fractions of monoclonal antibodies or surface proteins into the lipid bilayer of the liposome or chemical coupling of such compounds to the liposomal surface.

More preferably, the lipids and cholesterol are not subject to extrusion, i.e. the process does not comprise an extrusion step. By "extrusion" is meant a conventional technique for the preparation of liposomes, where a liposomal formulation is passed through a membrane of defined pore size. Extrusion processes have been discussed in the art as being the method of choice for liposome production (Gim Ming Ong et al., Evaluation of Extrusion Technique for Nanosizing Liposomes, Pharmaceutics 2016 (8) 36; Perrie et al., Manufacturing Methods for Liposome Adjuvants, in; Vaccine Adjuvants: Methods and Protocols, Methods in Molecular Biology, vol. 1494, 2017).

It has been found that liposomes produced by sonication according to this invention are smaller, less polydisperse, more stable and less prone to degradation than liposomes obtainable by conventional techniques.

Preferably, the aqueous solution in step b) is an aqueous buffer solution. Upon adding the aqueous liquid, the solved lipids and cholesterol precipitate. The final ratio of organic solvent in step a) and the aqueous liquid in step b) may be 1:9, meaning that the organic solvent is 10% of the total liquid mixture. Too high solvent concentration in the end product can lead to liposomal instability and/or degradation.

The sonication is preferably performed with an amplitude of at least 60 μm and for at least 1 hour. The sonication can be performed up to 24 hours.

The separation step can be achieved by centrifugation; filtration; field flow fractionation (FFF); dialysis; chromatographic methods, preferably gel-permeations-chromatography.

The liposomes are separated from remaining substances of the liquid mixture, such as organic solvent, salts and/or detergents. Preferably, step d) is performed by buffer exchange. Preferably, steps c) and d) do not require extrusion or any other separation method for the generation of a homogenous liposomal distribution. It is preferred that the liposomes are kept in the original mixture.

The liposome distribution is preferably at least 90% unilamellar and most preferably between 97% and 99% unilamellar. Preferably, the liposomes hold a circularity of 0.95 and most preferably between 0.98 and 1.00. Circularity and the lamellarity have been determined based on images recorded with a cryoTEM JEOL JEM-2100F. In liposomal formulations according to the invention, the ratio of spherical liposomes to broken particles and/or aggregates in weight-% is higher than 9:1, measured by cryotransmission electron microscopy.

The method has the advantage, that small homogeneous liposome can be obtained in one sonication step avoiding thin-film hydration and extrusion and other elaborated and costly steps. Liposomes with a mean diameter of less than 50 nm have a higher tendency to be stable and to cross the blood-brain barrier. In other words, the passing of the blood-brain barrier is facilitated by the small diameter of the liposomes.

At least a part of the lipids used in step a) may be chosen from the group: phospholipids, natural phosphatidylcholine and in particular sphingomyelin; glycolipids, in particular ganglioside; and a combination thereof. It is also possible to use further components such as cholesterol which greatly contribute to the liposomal stability.

These lipids have the advantage of being stable and resistant. Further, they are biocompatible.

Preferably, the organic solvent used in step a) is chosen from the group, consisting of: ethanol, methanol, chloroform and mixtures thereof. Most preferably, organic solvents with high degree of purity are used, e.g. ethanol or methanol absolute >99.99%. Even more preferably, no thin-film hydration is needed.

The used lipids show a good solubility in these organic solvents. By using organic solvents with a high degree of purity contamination of the liposomes with impurities is avoided.

The aqueous liquid used in step b) may be chosen from the group, consisting of: water, aqueous buffer solution, aqueous glycine-solution. Preferably, aqueous buffer solutions with a physiological salt concentration, e.g. PBS (10 mM phosphate, pH 7.2-7.4, 0.9% NaCl) can be used. It is also possible to use the following aqueous buffer solutions: 150 mM ammonium sulphate, 150 nm calcium acetate, 150 mM magnesium acetate, 150 mM manganese acetate, 150 mM iron chloride, or 150 mM copper sulphate.

The aqueous liquid enhances the liposome formation. By using physiological salt concentration, the interior of the liposome resembles the physiological conditions in the body.

Preferably, the organic solvent used in step a) and/or the aqueous liquid used in step b) comprise an active component. The active component is preferably chosen from the groups previously described. The active component is incorporated to the aqueous phase or the solvent, depending on their chemical properties.

It is also possible, that the organic solvent comprises a first active component and the aqueous liquid comprises a second active component. These components may be chosen such that they show a synergistic effect.

A further advantage of having an organic and an aqueous solvent present in the preparation method of the liposomes can be found in a broader access towards active components. Components with a higher solubility in the organic solvent than the aqueous liquid may be equally used and vice versa.

Preferably, the active component should fulfil the following criteria:
show an amphiphilic solubility in water, meaning having a log D value between −2 and +2,
comprise at least one weak acid- or base group.

Under certain conditions, it may also be possible to use active components with a log D value >+2. Substances having a log D between −2 and +2 can be encapsulated by remote loading. Molecules with a log D beyond this range may be loaded by membrane encapsulation.

The use of an additionally active component enhances the therapeutic effect. Due to their similarity with cell membranes, the liposomes may merge with the cell membrane and may specifically act as an active component at the target site. The liposomes may also release the encapsulated or comprised active components into the cell after merging of the liposome with the cell membrane.

The liposomes as previously described may be used as a medicament, in particular for use in the treatment of neurodegenerative diseases and spinal cord injuries.

The neurodegenerative disease may be chosen from the group as previously described. The spinal cord injuries refer to all types of spinal cord injuries.

Preferably, the liposomes as previously described, in the treatment of neurodegenerative diseases and spinal cord injuries as previously described, are administered orally or intravenously.

If administered orally, the liposome composition can be in form of a solid or a drinkable solution. It may be in the form of dragees, tablets, granulate, capsules, powder, an emulsion, suspension or syrup. The liposomes as previously described have the advantage of having a stability resisting the conditions associated with passing the gastrointestinal passage. By oral administration, side effects associated with a subcutaneously or intravenously delivery can be avoided.

Further, if administered orally, the liposomal composition can include further ingredients. The addition of flavours would provide a more pleasant taste, enteric coatings e.g. on the tablets would provide an additional protection against the acid. Basic ingredients such as hydrogen carbonate may provide a stomach-friendly administration. Also vitamins or minerals could be included.

The oral administration has the advantage of being easier applicable than intravenously. A patient would be able to take the medicament in accordance with the prescription and without the need of trained personal.

An intravenous administration can be of advantage if uptake of the liposomes through the gastrointestinal track is less favoured, for example due to the patient's health condition.

For intravenous injection, the liposomes may be present in solved or suspended form. The amount of liquid may be in the range of 0.1-20 ml and is dose dependent. The injectable solution can comprise further ingredients, such as stabilising agents. It can also comprise physiological compatible ingredients such as salt, in particular sodium chloride or alcohol, preferably ethanol.

A further aspect of the invention is liposomes as previously described obtainable by a method as previously described.

The invention will be further outlined in the following.

Figure 1:
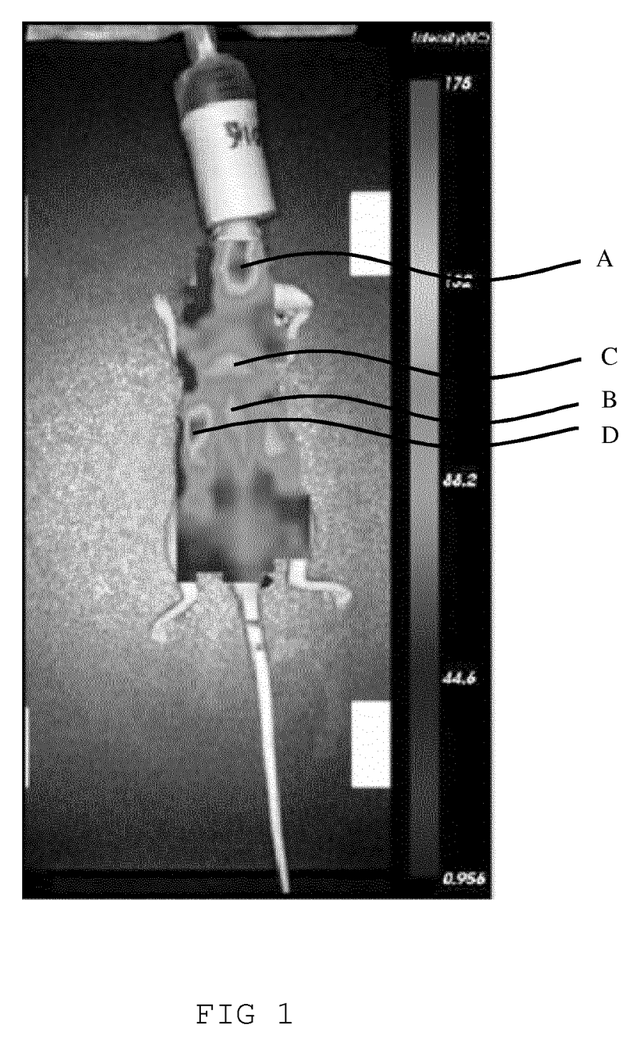
FIG. 1: In vivo biodistribution of liposomes comprising sphingomyelin labelled with ICG according to the invention.
Figure 11:
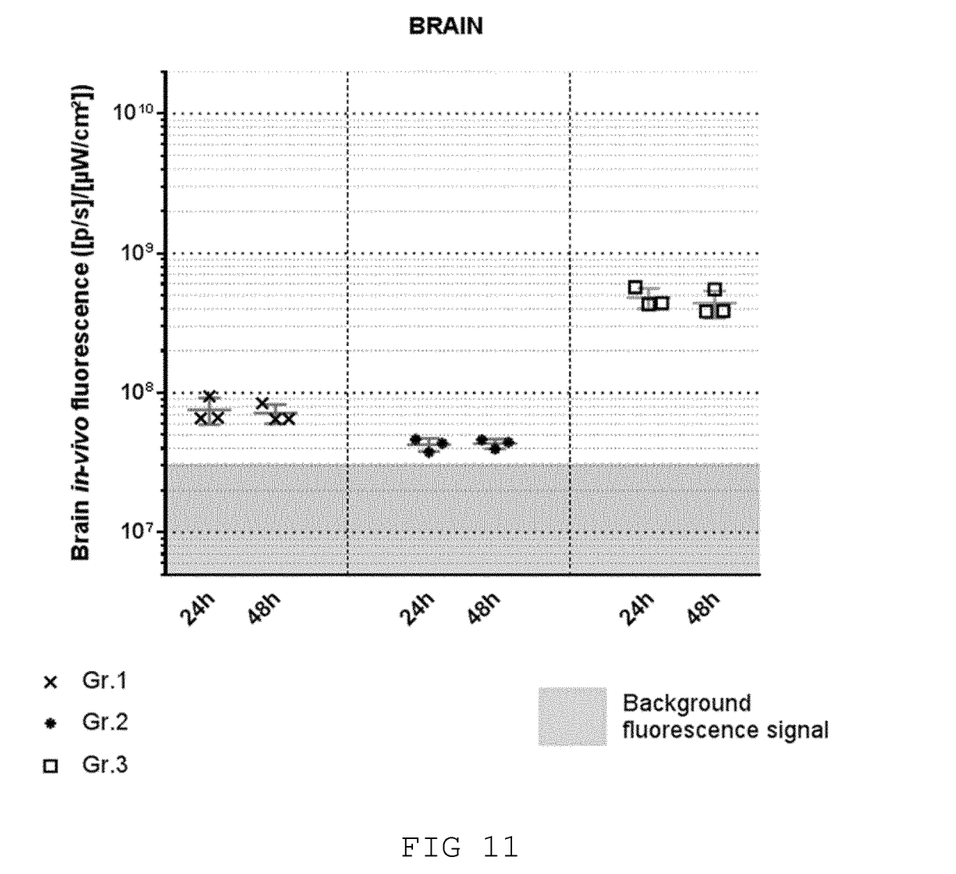

FIG. 11: In-vivo fluorescence of liposomal formulations with different lipid compositions in the brain FIG. 1 shows the in vivo biodistribution of sphingomyelin liposomes labelled with Indocyaninegreen (ICG). Mice were treated intravenously with liposomes carrying near-infrared dye and biodistribution was analysed 24 hours post-injection. Analysis was performed with a GE HealthCare eXplore Optix. Signals of the ICG were found in brain (A) and the spinal cord (B). Total liposome lipid injection was 45 mg/kg carrying 1:200 weight-to-weight ICG. Further signals could be found in the clearance organs liver (C) and spleen (D), indicating that after treatment the liposomes can be removed from the body.

Figure 2:
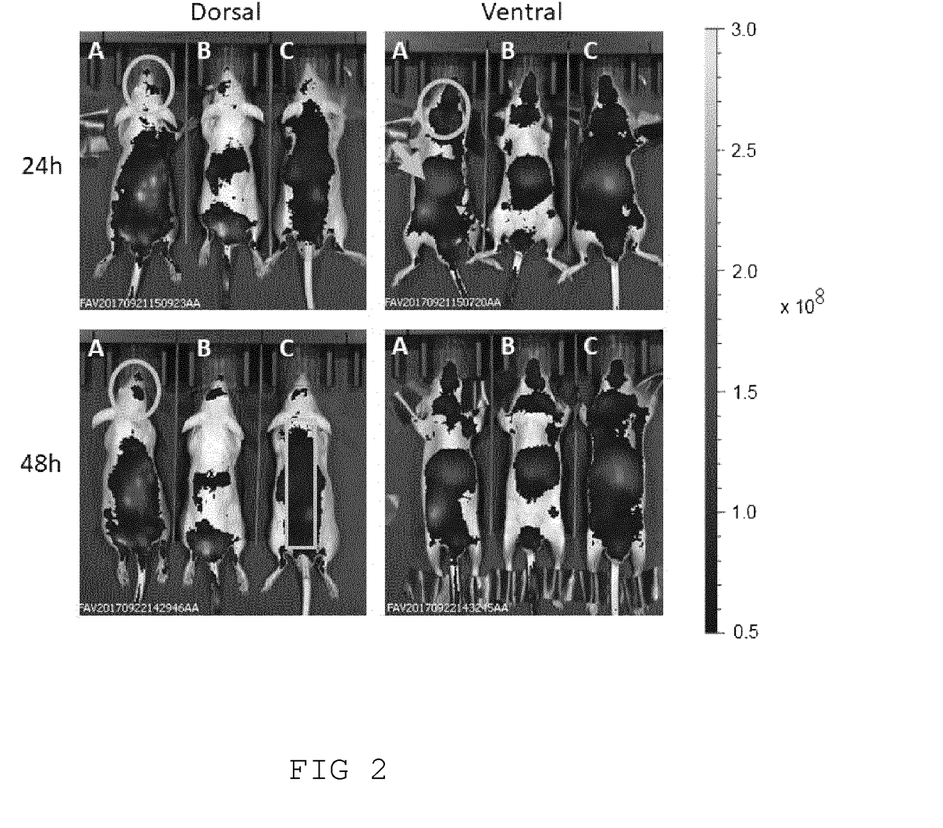
FIG. 2: In vivo biodistribution of liposomes comprising sphingomyelin labelled with DiR according to the invention.

FIG. 2 shows the in vivo biodistribution of sphingomyelin liposomes labelled with DiR. Different mice A, B, C were treated intravenously with liposomes carrying near-infrared dye and biodistribution was analysed 24 and 48 hours post-injection in a ventral view and a dorsal view. Analysis was performed with an optical imaging system, IVIS Spectrum of Perkin Elmer. Signals of the DiR were found in the brain (circle) and spinal cord (rectangle). Total liposome lipid injection was 15 mg/kg carrying 50 µg/ml DiR. Further signals could be found in the clearance organs liver (plain arrow) and spleen (doted arrow), indicating that after treatment the liposomes can be removed from the body. The fluorescence scale is termed in the following unit: total Radiant efficiency $[p/s]/[\mu W/cm^2]$.

Figure 3:
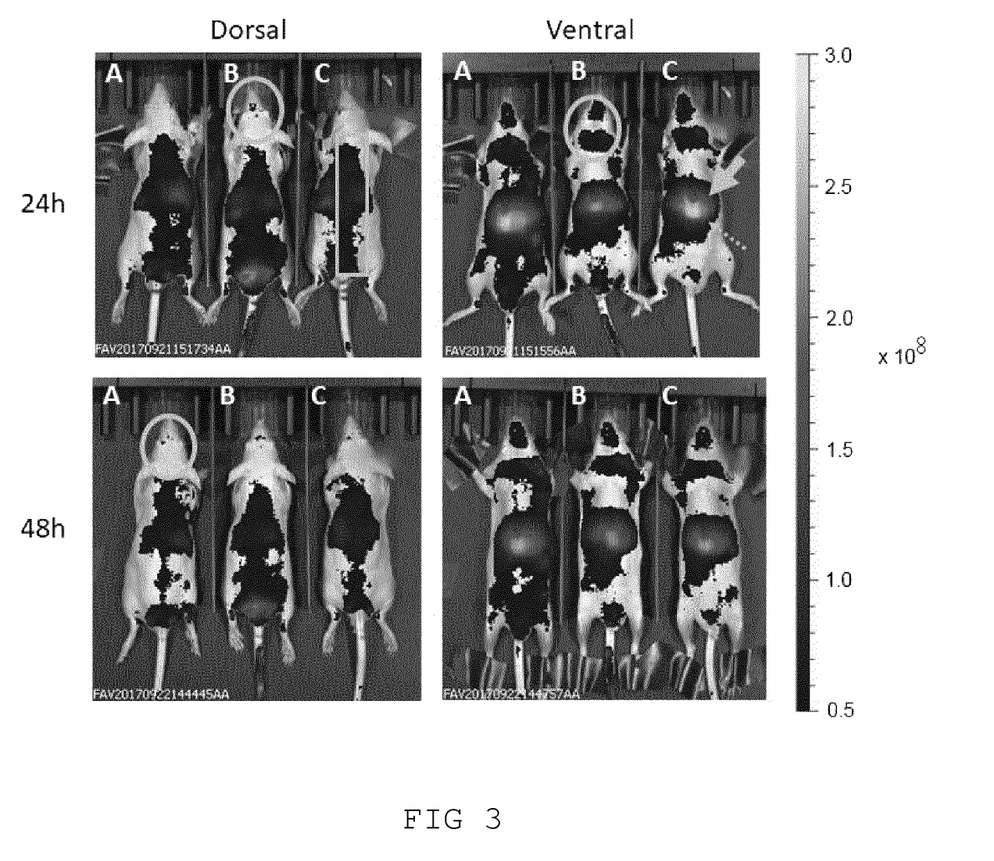
FIG. 3: In vivo biodistribution of liposomes comprising sphingomyelin and GM1 labelled with DiR as comparative example to FIG. 2.

FIG. 3 shows a comparative example of the in vivo biodistribution of a liposome with sphingomyelin and GM1, labelled with DiR. Mice were treated intravenously with liposomes carrying near-infrared dye and biodistribution was analysed 24 and 48 hours post-injection. Analysis was performed with an optical imaging system, IVIS Spectrum of Perkin Elmer. Signals of the DiR were found in brain (circle) and the spinal cord (rectangle). Total liposome lipid injection was 25 mg/kg carrying 50 µg/ml DiR. Further signals could be found in the clearance organs liver (plain arrow) and spleen (doted arrow), indicating that after treatment the liposomes can be removed from the body. The fluorescence scale is termed in the following unit: total Radiant efficiency $[p/s]/[\mu W/cm^2]$. Even though the liposomes are found in the same organs as the liposomes presented in FIG. 2, the biodistribution is less distinct compared to the essentially GM1-free liposomes in FIG. 2.

FIG. 4 shows a graphic representation of the biodistribution analysis in the brain, spinal cord, liver and spleen from the in vivo biodistribution images of FIG. 2 and FIG. 3. FIG. 4A shows the normalised fluorescence of the biodistribution of the liposome without ganglioside in four different tissues: brain, spinal cord, liver and spleen. The biodistribution is displayed for two different time points: 24 and 48 hours. The bars represent the standard deviation to the mean. FIG. 4B shows the normalised fluorescence of the biodistribution of the liposome with ganglioside.

It was surprisingly found, that the in vivo biodistribution of the liposome essentially lacking ganglioside (FIG. 4A) is higher than the in vivo biodistribution of the liposome comprising ganglioside (FIG. 4B).

Figure 5:
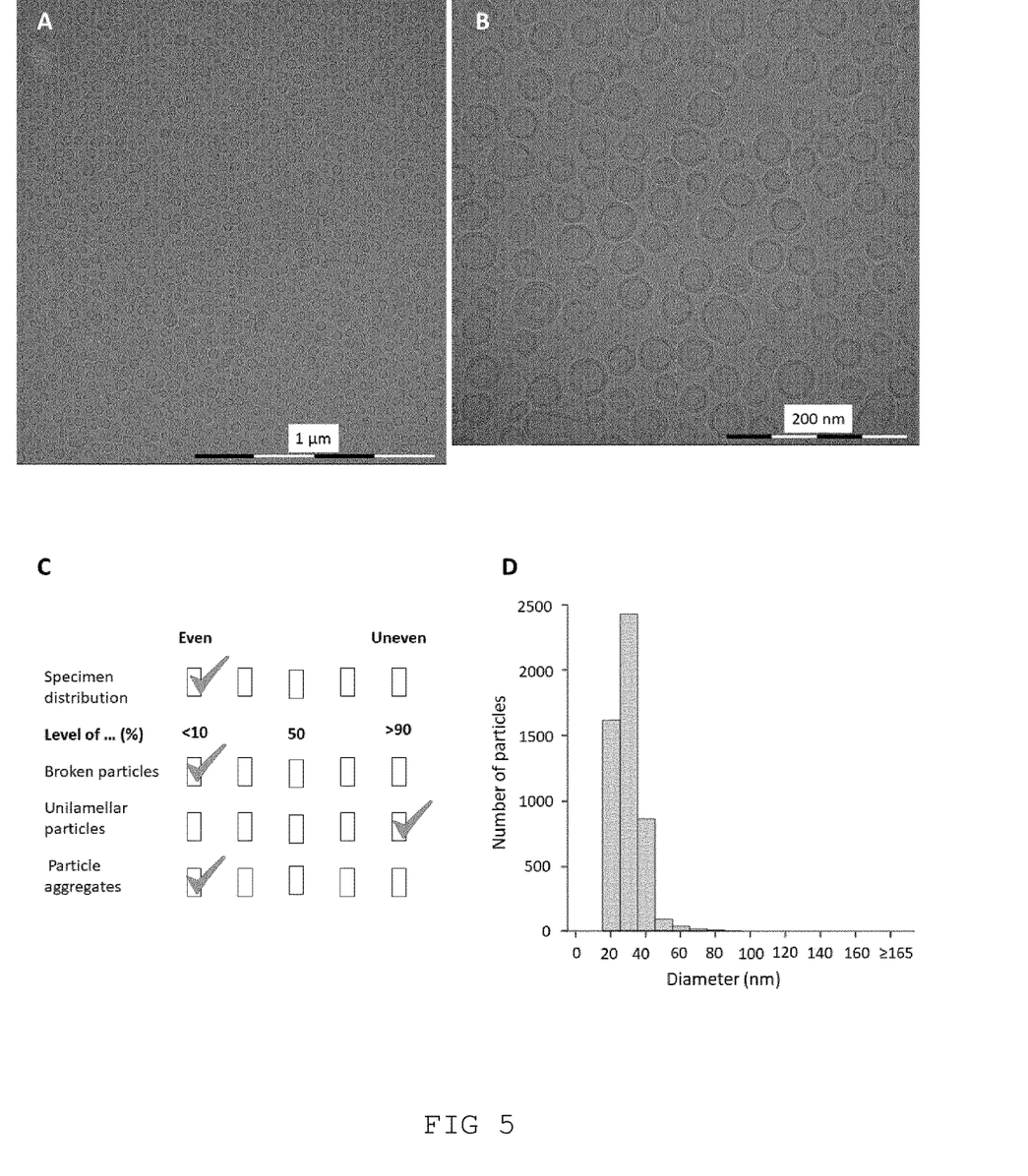
FIG. 5: Characterization of the liposomes without surface modification by cryoTEM: (A) Visualization low magnification, (B) Visualization high magnification, (C) Qualitative assessment, (D) Quantitative diameter distribution.

FIG. 5 shows the characterization of the liposomes without surface modification. liposomes were visualized using Cryo Transmission Electron Microscope JEOL JEM-2100F and a TVIPS Tem-Cam camera (JEOL Ltd., Japan). FIG. 5A shows an image of the liposomes at low magnification (20000×). FIG. 5B shows the liposomes at high magnification (80000×). FIG. 5C shows a qualitative assessment done by ocular/visual observation of the liposomal distribution. FIG. 5D shows the size distribution of the liposomes of this invention. In order to quantify the mean diameter of the liposomes N(liposomes)=5128 were analysed (Vironova Analyzer Software, Vironova, Sweden). The mean diameter of the liposomes is 30.46 nm with a standard deviation of 10.10 nm.

Figure 6:
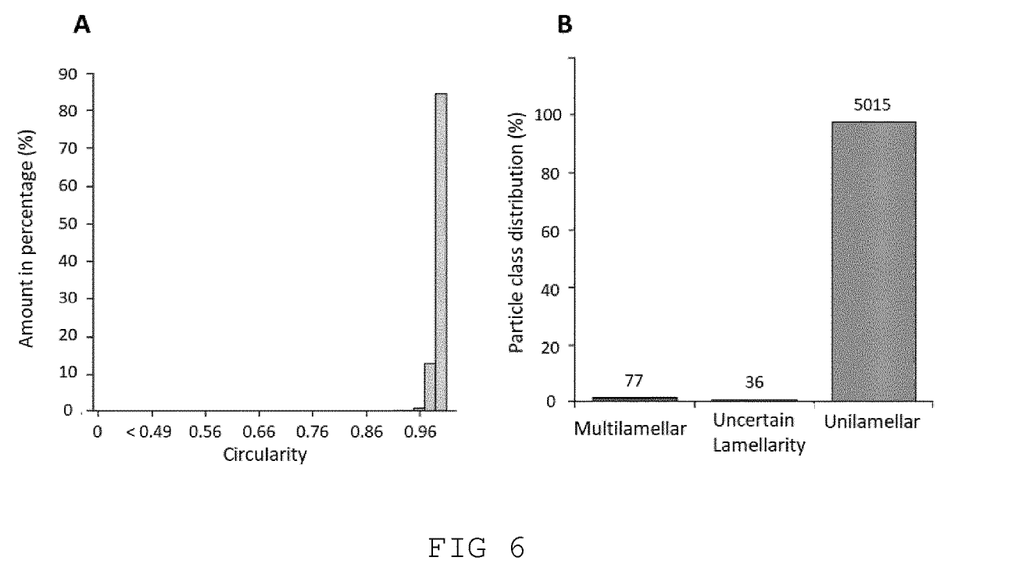
FIG. 6: Quantitative characterisation of the liposomes without surface modification by cryoTEM. (A) circularity distribution, (B) lamellarity diagram.

FIG. 6 comprises two further tests for a quantitative characterisation of the liposomes without surface modification by cryoTEM (Vironova Analyzer Software, Vironova, Sweden). FIG. 6A shows the circularity distribution of 5128 liposomes. FIG. 6B shows the lamellarity grade of the liposomal distribution. 98% of 5128 liposomes have been characterised as unilamellar.

FIGS. 7 and 8 show the size and polydispersity stability of liposomes according to the invention over time, measured by dynamic light scattering. The liposomal formulations were obtained according to the method described above, by using sphingomyelin and cholesterol in a 1:1 molar ratio. The liposomes were completely free of gangliosides, surface modifications, and did not comprise or encapsulate an active component. The liposomal formulations were stored in PBS at a pH-value of 6.8 and a temperature of 4° C. Size and polydispersity were determined by DLS standard methods. It shall be noted that the values measured by dynamic light scattering are slightly higher than the values obtainable by cryoTEM due to the impact of the hydrodynamic radius of liposomes on DLS measurements. A diameter of 60 nm as indicated in FIG. 7 corresponds to a mean diameter in the range of 10 and 50 nm when measured by Cryo Transmission Electron Microscopy.

The dotted curve shows the results of a small scale production batch of liposomal formulation as described above, while the dashed curve shows the results of an upscale production, i.e. a batch size of 2 litres. As can be seen from FIGS. 7 and 8, both the size and polydispersity of the liposomal formulations from Q3 2017 to Q3 2018, i.e. during storage time of one year, remained essentially unchanged.

Figure 9:
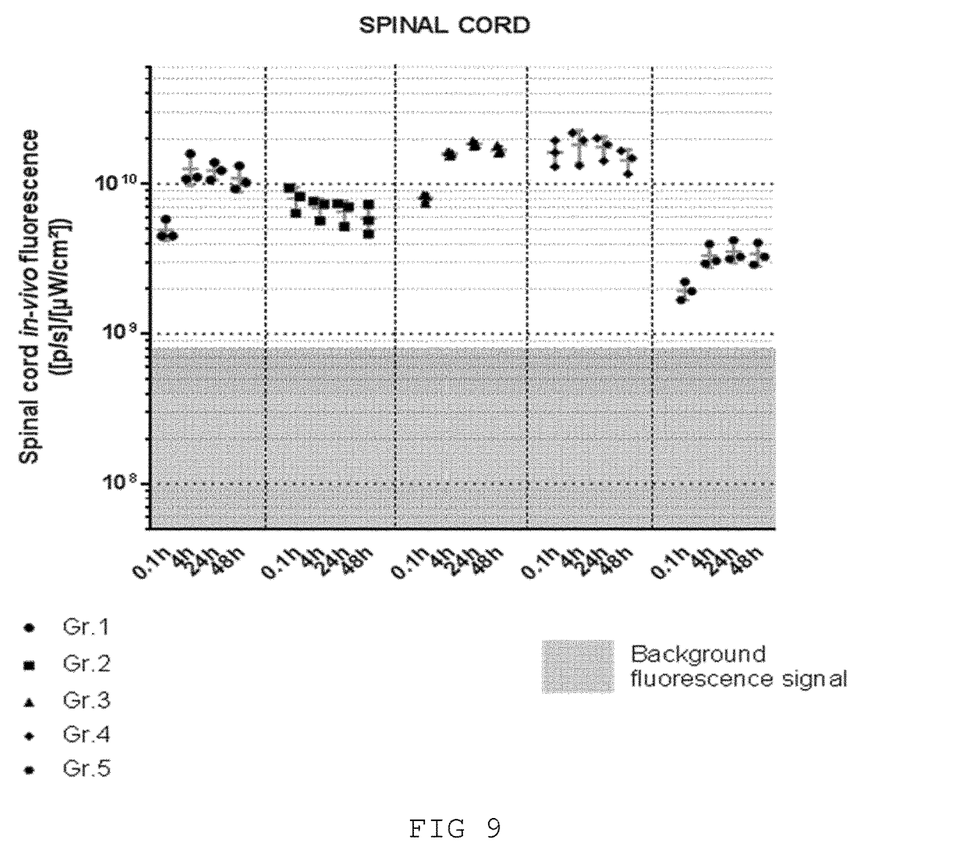
FIGS. 9/10: In-vivo fluorescence of different liposomal formulations in spinal cord and brain.
Figure 10:
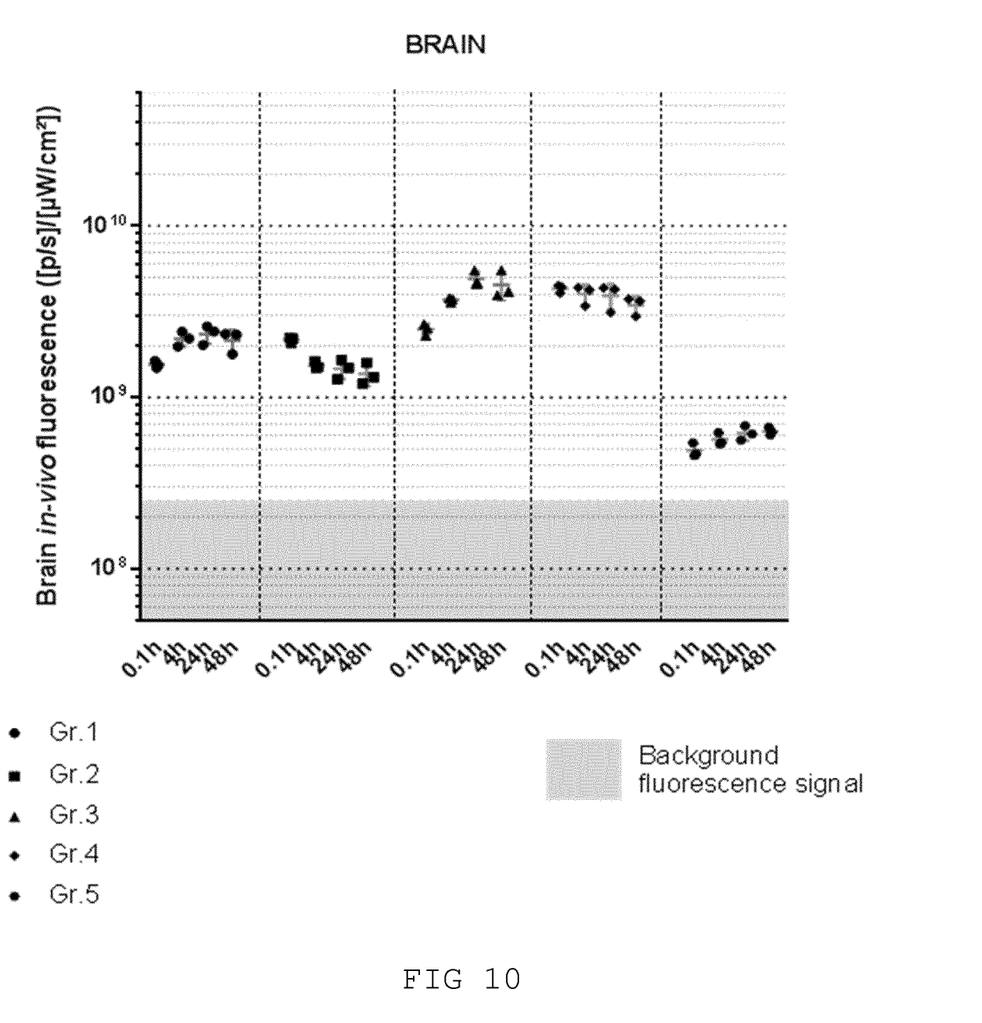

FIGS. 9 and 10 show relative in-vivo fluorescence of different liposomal formulations in the spinal cord and brain of mice. In both charts, the liposomes of groups 1 to 4 were obtained according to the method described above, by using only sphingomyelin and cholesterol in a 1:1 molar ratio. Gr. 5 is a control group of free DiR in PBS. In Gr. 1, synthetic sphingomyelin was used and GM1 was comprised in the liposomes. In Gr. 2, synthetic sphingomyelin was used and the liposome was completely free from surface modifications, in particular free from GM1. In Gr. 3, sphingomyelin of animal origin was used and GM1 was comprised in the liposomes. In Gr. 4 sphingomyelin of animal origin was used and the liposome was completely free from surface modifications, in particular free from GM1. For all four test groups, DiR was added as a labelling agent. The measurements were performed by NIR imaging technique.

FIGS. 9 and 10 show the accumulation of the four different kinds of liposomes in the spinal cord and brain respectively in 0.1 h, 4 h, 24 h and 48 h post-injection. It can be seen that the presence of GM1 does not significantly affect the ability of the liposomes to target the central nervous system. The same holds true for the use of synthetic sphingomyelin compared to the use of sphingomyelin of animal origin.

FIG. 11 shows the relative in-vivo fluorescence of liposomal formulations with different lipid compositions in the brain of mice. The liposomes of groups 1 to 3 were obtained according to the method described above by using lipids and cholesterol in a 1:1 molar ratio. In group 1, phosphatidylcholine and sphingomyelin in combination were used as lipids. In group 2, phosphatidylcholine alone was used as a lipid. In group 3, sphingomyelin alone was used as a lipid. In all three test groups, DiR was added to the formulations as a labelling agent. The measurements were performed by NIR imaging technique.

FIG. 11 shows the accumulation of the three different kinds of liposomes in the brain of mice after 24 h and 48 h post-injection. It can be seen that the composition consisting of sphingomyelin and cholesterol alone results in superior longevity of circulation and CNS bioavailability of the liposome compared to the other variants (Grps 1 and 2).

The invention claimed is:

1. Liposomes comprising:
   a lipid bilayer comprising sphingomyelin, and
   an inner aqueous compartment;
   wherein the lipid bilayer is essentially free of ganglioside,
   wherein the liposomes are completely free of surface modifications,
   wherein the liposomes have a mean diameter between 10 and 50 nm, and
   wherein the liposomes are capable of crossing the blood brain barrier.

2. The liposomes according to claim 1, wherein the liposomes additionally comprise cholesterol.

3. The liposomes according to claim 1, further comprising at least one active component which is optionally encapsulated in the inner aqueous compartment of the liposomes.

4. The liposomes according to claim 3, wherein the active component is selected from the group consisting of:
   cholinesterase-inhibitors;
   dopamine agonist;
   resveratrol; and
   nicotinic derivatives.

5. The liposomes according to claim 3, wherein at least one active component comprises gangliosides, and wherein the gangliosides are encapsulated in the inner aqueous compartment of the liposome.

6. The liposomes according to claim 1, contained in a liposomal formulation, wherein the liposomal formulation has a polydispersity index <0.15.

7. The liposomes according to claim 1, contained in a liposomal formulation, wherein the liposomes of the liposomal formulation have a mean relative circularity of 0.98 to 1.

8. The liposomes according to claim 1, wherein the liposomes are contained in a liposomal formulation, wherein at least 90% of the liposomes of the liposomal formulation are unilamellar.

9. The liposomes according to claim 3, wherein the liposomes are utilized as a medicament.

10. The liposomes according to claim 3, for the treatment of amyotrophic lateral sclerosis, wherein the treatment comprises the oral or intravenous administration of the liposomes.

11. The liposomes according to claim 1, wherein the liposomes are obtained by:
  a) providing lipids and cholesterol in an organic solvent,
  b) adding an aqueous liquid, and
  c) sonicating to enable liposome formation.

12. A method for producing the liposomes of claim 2, comprising:
  a) providing lipids and cholesterol in an organic solvent wherein the lipids include sphingomyelin,
  b) adding an aqueous liquid, and
  c) sonicating to enable liposome formation.

13. The method according to claim 12, wherein the organic solvent used in a) is selected from the group consisting of:
  ethanol,
  methanol,
  chloroform, and
  mixtures thereof.

14. The method according to claim 12, wherein the aqueous liquid used in b) is selected from the group consisting of:
  water,
  aqueous buffer solution, and
  aqueous glycine-solution.

15. The method according to claim 12, wherein at least one of the organic solvent and the aqueous liquid comprises an active component.

16. The method according to claim 15, wherein the method is for producing liposomes for the treatment of neurodegenerative diseases and spinal cord injuries.

* * * * *